United States Patent [19]
Ligon, Jr.

[11] Patent Number: 5,583,050
[45] Date of Patent: Dec. 10, 1996

[54] METHOD FOR PYROLYSIS

[75] Inventor: Woodfin V. Ligon, Jr., Schenectady, N.Y.

[73] Assignee: General Electric Company, Schenectady, N.Y.

[21] Appl. No.: 409,238

[22] Filed: Mar. 24, 1995

Related U.S. Application Data

[62] Division of Ser. No. 222,043, Apr. 4, 1994, Pat. No. 5,437,839.

[51] Int. Cl.$^6$ .................................................. G01N 31/12
[52] U.S. Cl. ........................ 436/155; 436/160; 436/178; 436/181
[58] Field of Search ............................ 30/115–117, 140; 83/200.1, 651.1, 914, 915.3; 144/364, 380; 431/128, 132, 262, 259; 422/78, 80, 89; 436/155, 160, 178, 181

[56] References Cited

U.S. PATENT DOCUMENTS

| | | | |
|---|---|---|---|
| 3,064,111 | 11/1962 | Newman | 30/116 |
| 3,985,505 | 10/1976 | Bredaweg | 422/28 X |
| 4,018,117 | 4/1977 | Patterson | 83/651.1 X |
| 4,779,497 | 10/1988 | Lee | 83/651.1 X |
| 5,178,837 | 1/1993 | Grisp | 422/78 |

FOREIGN PATENT DOCUMENTS

| | | | |
|---|---|---|---|
| 6-3351 | 1/1994 | Japan . | |
| 6-3347 | 1/1994 | Japan | 422/78 |
| 6-3350 | 1/1994 | Japan | 422/78 |
| 1321225 | 6/1973 | United Kingdom . | |

OTHER PUBLICATIONS

H. McCormick *J. Chromatog.* 1969, 40, 1–15.
M. Ryska et al. *Chem. Abstr.* 1974, 80, 121465r.
M. A. Posthamus et al. *Chem. Abstr.* 1975, 83, 174973y.
H. R. Schulten et al. *Chem. Abstr.* 1981, 94, 209354d.
M. G. Kontoming et al. *Instrum. Anal. Foods: Recent Prog. Proc. Symp. Int. Flavor Conf.* 3rd 1983, 1, 391–404.
C. Reddmann et al. *Labor Praxis* 1985, 9, 454–456, 458, 460–61.
A. Dross et al. *Fresenius Z. Anal. Chem.* 1987, 328, 495–498.
S. L. Hathcock et al, *J. High Res. Chromatog.* 1993, 16, 609–614.
J. P. Dworzanski et al. *Appl. Environ. Microbiol.* 1990, 56, 1717–1724.
S. L. Hathcock et al. *Chem. Abstr.* 1994, 120, 85017e.
S. Hathcock et al. *Chem. Abstr.* 1994, 120, 115534r.

*Primary Examiner*—Arlen Soderquist
*Attorney, Agent, or Firm*—William H. Pittman

[57] ABSTRACT

By heating a wire and positioning the wire against a specimen, the specimen may be pyrolyzed to release a pyrolysate therefrom. The pyrolysate is collected in a hood and carried to a membrane separator from which the pyrolysate may be spectrochemically analyzed. The heated wire may be repeatedly indexed for replacing the adulterated portion of the wire with a clean portion of the wire for each subsequent pyrolysis and spectrochemical analysis of the pyrolysate therefrom. A pyrolysis instrument includes a movable probe supporting the heated wire with the probe being preferably joined to a remote membrane separator flexibly joined thereto.

3 Claims, 6 Drawing Sheets

5,583,050

METHOD FOR PYROLYSIS

This application is a division of application Ser. No. 08/222,043, filed Apr. 4, 1994, now U.S. Pat. No. 5,437,839.

BACKGROUND OF THE INVENTION

The present invention relates generally to infrared spectroscopy and mass spectrometry, and, more specifically, to pyrolysis of polymer specimens for analysis therein.

In order to effectively recycle plastic or polymeric parts such as engineering thermoplastics found in an automobile, the type of polymer must be identified in order to segregate parts made from the same material. In an industrial recycling plant, the different plastic parts must be properly identified and segregated for cost efficiency. Segregation of the parts may be accomplished by visual identification where possible, and where not possible, the parts must be suitably analyzed to determine the chemical composition thereof.

Pyrolysis of polymers or plastics followed by conventional spectrochemical analysis is one conventional approach for determining chemical composition of an analyzed specimen. In pyrolysis, a specimen in the form of a small sample is suitably heated in an air environment for obtaining chemical decomposition thereof and the release of pyrolysis products which are volatile heated vapors also referred to as pyrolysate. The pyrolysate is then carried by the air to an infrared spectrometer for the conventional chemical analysis thereof. The pyrolysate may also be analyzed in a conventional mass spectrometer to determine the chemical composition. However mass spectrometers typically require an inert gas such as helium for transporting the pyrolysate therein, in which case a conventional separator membrane is typically used to transfer the pyrolysate from the heated air through the membrane to the helium on the other side thereof. An exemplary membrane includes a layer of silicone sandwiched between two stainless steel wire meshes in a flat disk form which can be suitably mounted in a housing.

In view of the complexity of the conventional equipment used in pyrolysis and infrared or mass spectrometry, the use thereof in a high speed, high volume plastics recycling plant is not practical.

SUMMARY OF THE INVENTION

By heating a wire and positioning the wire against a specimen, the specimen may be pyrolyzed to release a pyrolysate therefrom. The pyrolysate is collected in a hood and carried to a membrane separator from which the pyrolysate may be spectrochemically analyzed. The heated wire may be repeatedly indexed for replacing the adulterated portion of the wire with a clean portion of the wire for each subsequent pyrolysis and spectrochemical analysis of the pyrolysate therefrom. A pyrolysis instrument includes a movable probe supporting the heated wire with the probe being preferably joined to a remote membrane separator flexibly joined thereto.

BRIEF DESCRIPTION OF THE DRAWINGS

The invention is more particularly described in the following detailed description taken in conjunction with the accompanying drawings in which.

DESCRIPTION OF THE PREFERRED EMBODIMENT(S)

Figure 1:
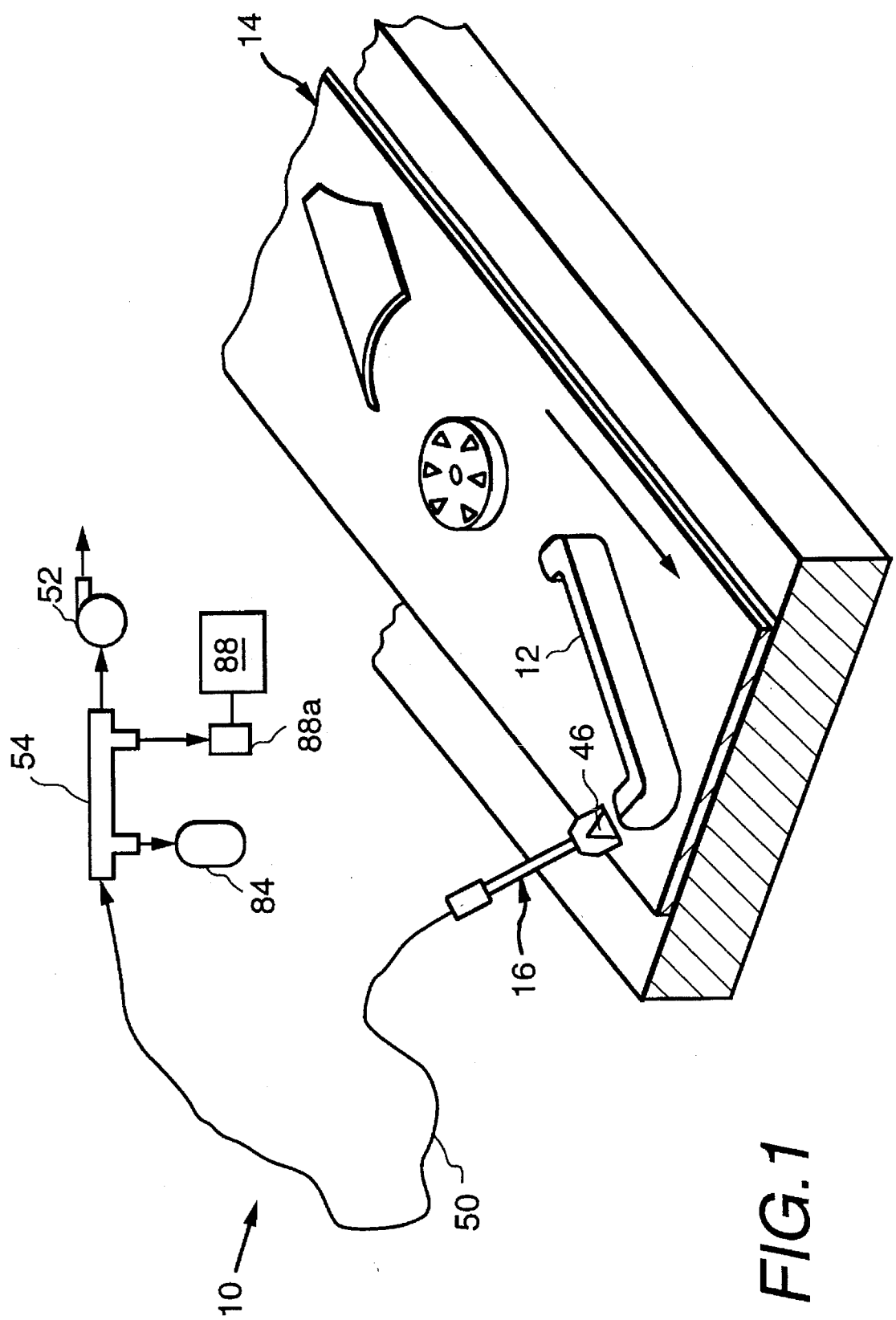
FIG. 1 is a schematic representation of an exemplary embodiment of a pyrolysis instrument including a membrane separator providing a pyrolysate to a spectrochemical analyzer from a specimen moving along a conveyor belt in an industrial recycling plant.

Illustrated schematically in FIG. 1 is a pyrolysis instrument 10 in accordance with an exemplary embodiment of the present invention for obtaining a pyrolysate sample from a plastic or polymeric specimen 12 such as an automobile bumper being carried along a conventional conveyor belt 14 in an industrial recycling plant. The conveyor belt 14 carries various plastic parts or specimens 12 such as the bumper illustrated, or hub caps, or various automobile body parts, or any other type of plastic parts which must be segregated according to composition. Some parts may be visually identified as having known compositions and thereby segregated if the part or its composition is unrecognized however, the pyrolysis instrument 10 may be manually or automatically used for obtaining a pyrolysate sample, or simply pyrolysate, therefrom and then analyzed using spectrochemical analysis to determine the chemical composition thereof.

Figure 2:
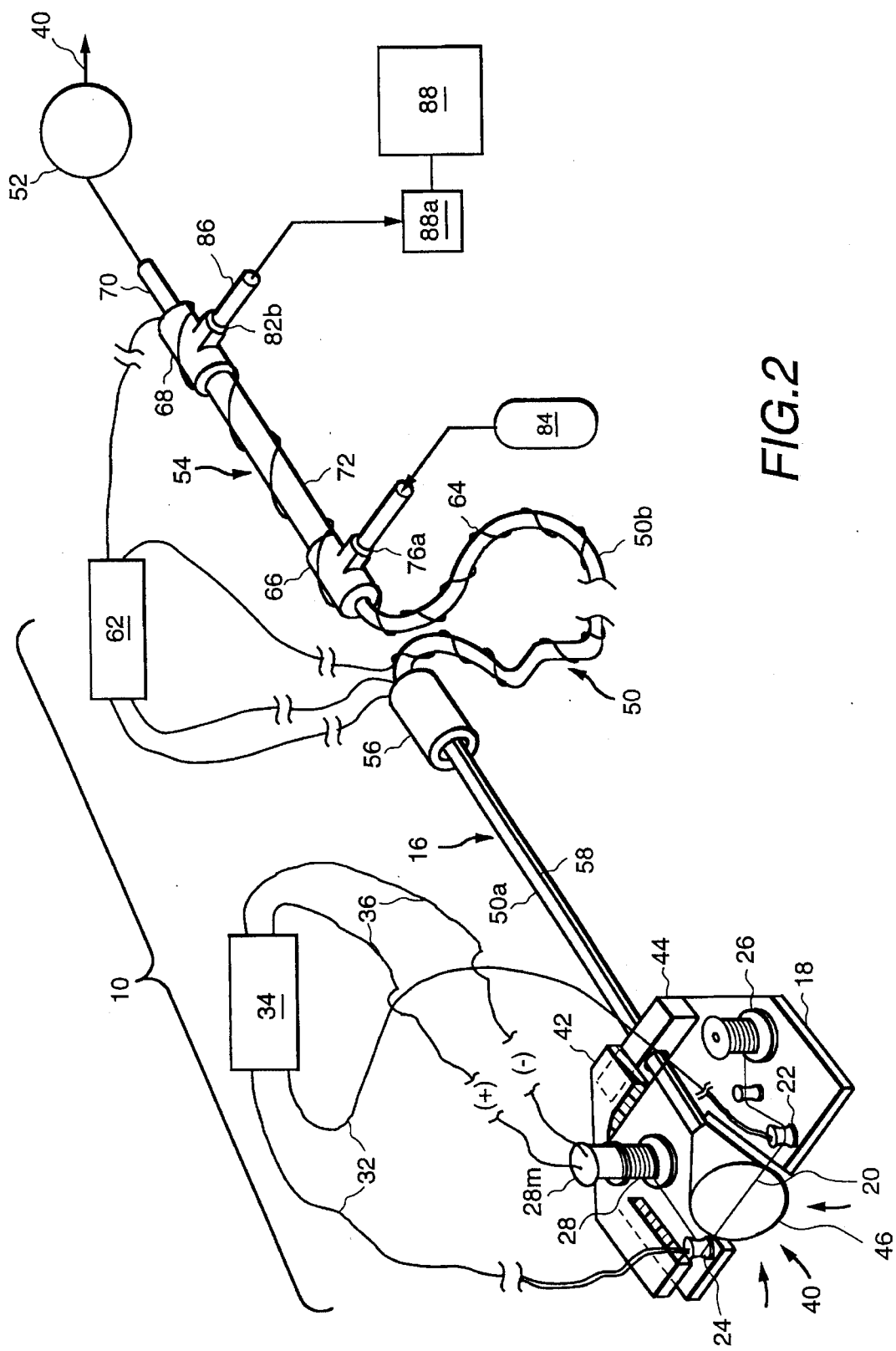
FIG. 2 is an enlarged, schematic representation of the pyrolysis instrument illustrated in FIG. 1 showing a movable probe flexibly joined to the membrane separator.

The pyrolysis instrument 10 is illustrated in more particularity in FIG. 2 and includes an elongate probe 16 which may be manually or automatically positioned adjacent to the specimen 12 for obtaining a pyrolysate therefrom. At one end, the probe 16 includes a base 18 in the form of a flat plate having a pyrolysis wire 20 supported thereon and positionable against the specimen 12 (see FIG. 1). Suitable means are provided for heating the wire 20 to a sufficiently high temperature to pyrolyze by cutting or melting a slice in the specimen 12 to release the pyrolysate therefrom in the form of heated vapors.

Since the heated wire 20 melts a portion of the specimen 12, it becomes contaminated or adulterated and must be changed for each subsequent pyrolysis. Accordingly, FIG. 2 illustrates additional means supported on the base 18 for indexing or moving into position another, clean portion of the wire 20 for use in effecting a subsequent pyrolysis on the next specimen 12.

Figure 3:
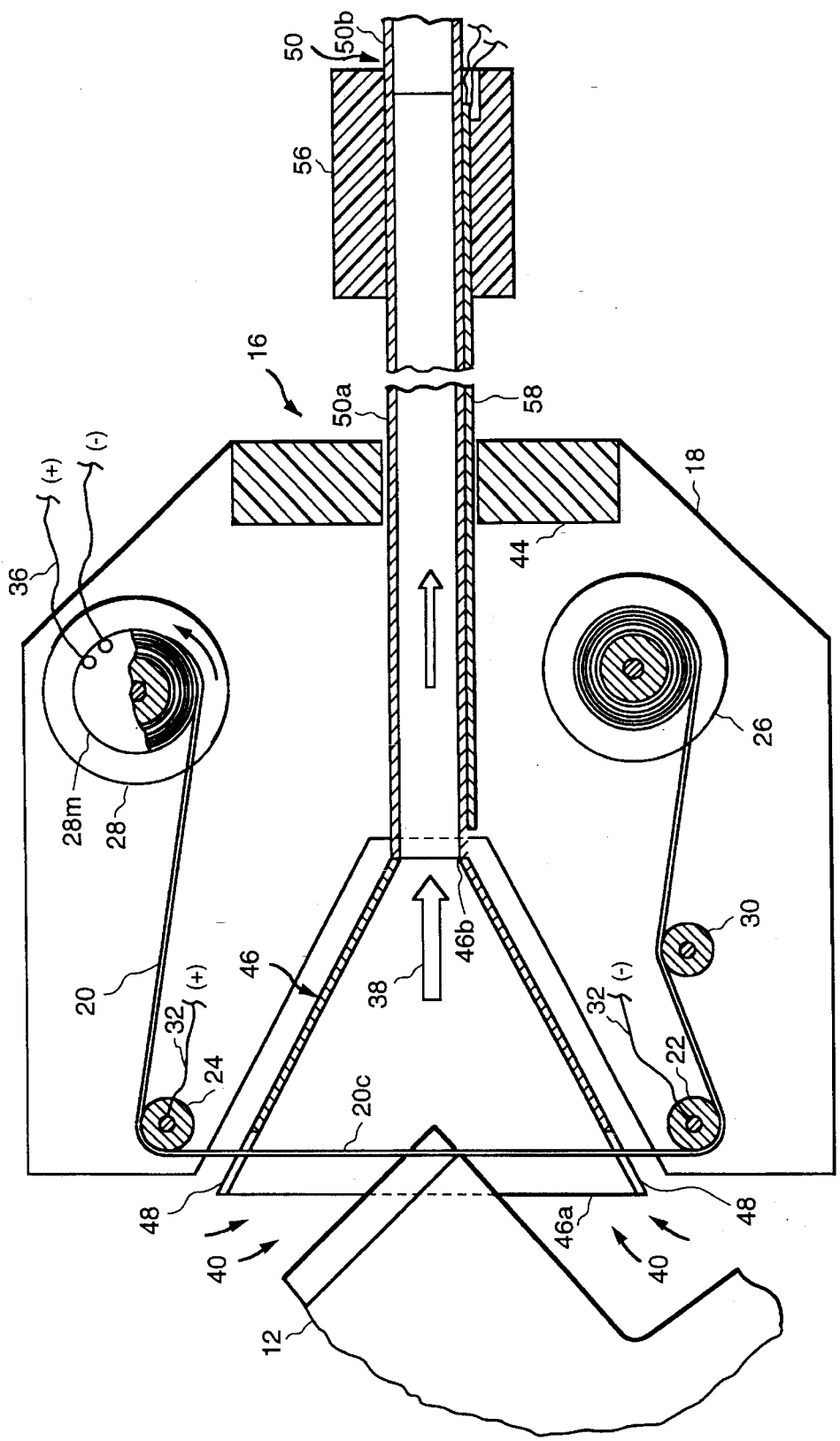
FIG. 3 is a partly sectional plan view of portions of the probe illustrated in FIG. 2.

More specifically, the wire indexing means is illustrated in more particularity in FIG. 3 and includes first and second pulleys 22, 24 which are suitably rotatably joined to the base 18 by center axles therein. The pulleys 22, 24 are spaced laterally apart from each other on the base 18 for supporting therebetween a cutting portion 20c of the wire 20. A feed reel or spool 26 is suitably rotatably joined to the base 18 by another axle therein, adjacent to the first pulley 22 and carries a predetermined length of the wire 20 which is stored thereon. The wire 20 extends from the feed reel 26 and in turn over the first and second pulleys 22, 24 and in turn to a suitably powered drive reel or spool 28. The drive reel 28 is rotatably joined to the base 18 by an axle therein and adjacent to the second pulley 24 for receiving and storing the wire 20 received therefrom during operation. The drive reel 28 preferably includes a low voltage, DC drive motor 28m which is effective for selectively or intermittently rotating the drive reel 28 when desired for winching the wire 20 to feed clean cutting portions thereof into position between the first and second pulleys 22, 24 from the feed reel 26. The spent or contaminated cutting portions 20c are wound or taken up and stored on the drive reel 28. A conventional idler pulley 30 or other suitable apparatus may be provided to ensure that the wire 20 is maintained relatively taut between the first and second pulleys 22, 24, with the drive reel 28 providing tension in the wire 20, with suitable resistance or reaction being provided by the feed reel 26.

Since the wire 20 intermittently moves during operation, suitable heating means are required for heating the cutting portion 20c to sufficiently high temperatures for pyrolyzing the specimen 12 upon contact therewith. As shown in FIG. 3, the heating means includes in an exemplary embodiment a pair of electrical conductors or wires 32 joined to respective ones of the first and second pulleys 22, 24 at the axles thereof for example. The first and second pulleys 22, 24 are therefore preferably made of electrically conductive metal for carrying current to the wire 20 disposed thereon. A suitable electrical power supply 34 shown in FIG. 2 is joined to the conductors 32 for carrying electrical current through the wire 20 preferably solely in the cutting portion 20c between the first and second pulleys 22, 24. In order to improve safety, the power supply 34 is preferably a low voltage, DC power supply, 6 volts for example, effective for suitably heating the wire cutting portion 20c to temperatures high enough to pyrolyze the specimen 12 upon contact therewith. The wire 20, accordingly, may be formed of a suitable heating material such as nichrome which is effective for resistance heating thereof while having suitable strength. In the preferred embodiment illustrated in FIGS. 2 and 3, the low voltage DC power supply 34 is also suitably electrically joined to the drive motor 28m by additional conductors 36 for powering said motor 28m and selectively rotating the drive reel 28 when desired by using a simple on-off switch for example.

Since electrical current is provided directly to the first and second pulleys 22, 24 for heating the wire cutting portion 20c to a suitably high temperature, the base 18 is preferably an electrical insulator having high temperature capability for accommodating the high temperature of operation of the wire cutting portion 20c joined thereto through the pulleys 22, 24. Suitable, conventional high temperature plastics may be used such as ULTEM polyimide which is available from the General Electric Company. A matching cover plate 42 of the same high temperature material as the base 18 is disposed parallel to the base 18 and suitably joined to the top ends of the first and second pulleys 22, 24 for providing additional support thereto, and is joined to a suitable block 44 at the aft end of the base 18 as illustrated in FIG. 2, also made of the same high temperature plastic. Suitable access holes are provided in the cover plate 42 for the feed and drive reels 26, 28 and the electrical conductors 32, 36.

As shown in FIG. 3, the heated wire cutting portion 20c vaporizes a cut into the specimen 12 which releases pyrolysate 38 in the form of heated vapors which may also include undesirable contaminates such as smoke particulates, water vapor, and $CO_2$ which result in part from the surrounding air 40 in the vicinity of the heated cutting wire portion 20c. In order to analyze the pyrolysate 38, means are provided for collecting the pyrolysate 38 produced from the pyrolysis of the specimen by the heated wire 20c, which in the exemplary embodiment illustrated in FIGS. 2 and 3 is a hood 46 in the exemplary form of a stainless steel funnel supported by the base 18. As illustrated in FIG. 3, the hood 46 has an inlet 46a at one end thereof across which the wire cutting portion 20c extends, and an outlet 46b at an opposite end thereof. In the exemplary form of the funnel illustrated in FIG. 3, the inlet 46a of the hood 46 is larger than the outlet 46b, and the hood 46 preferably includes a pair of opposing notches 48 at the inlet 46a for receiving or recessing without obstruction the wire cutting portion 20c extending between the first and second pulleys 22, 24. In this way, the cutting portion 40c is recessed partly into the hood 46 for better capturing the pyrolysate 38 released from the specimen 12.

As illustrated in FIG. 1, the exhaust hood 46 is joined to the end of the probe 16 and is therefore mobile in this embodiment. The pyrolysate 38 is channeled from the hood 46 through a transfer conduit 50 extending from the outlet 46b of the hood 46 (check 42/46 above) to a conventional air or vacuum pump 52 disposed in flow communication with the hood outlet 46b for drawing therefrom the pyrolysate 38 formed upon pyrolysis of the specimen 12 by the heated wire cutting portion 20c as shown in FIG. 3. As shown in FIG. 1, a membrane separator assembly 54 is preferably joined in flow communication between the transfer conduit 50 and the pump 52 for separating from the pyrolysate 38 gaseous contaminants therein such as water vapor and $CO_2$, and smoke particulate contaminants before analysis of the pyrolysate 38 itself.

The transfer conduit 50 is illustrated in more particularity in FIGS. 2 and 3 and includes a straight, rigid portion 50a which forms a handling shaft for the probe 16, and a flexible portion 50b extending rearwardly therefrom to the membrane separator 54 for allowing maneuverability of the probe 16 next to the conveyor belt 14. The rigid portion 50a is conventionally fixedly joined at one end to the base 18 of the probe 16 by being clamped by the block 44. The rigid portion 50a is suitably rigidly joined to the hood outlet 46b in flow communication therewith for receiving the pyrolysate 38 drawn therein from the vacuum created by the pump 52 for exhausting the pyrolysate 38 from the hood 46. The hood 46 is therefore fixedly joined to the base 18 by attachment to the end of the rigid portion 50a of the transfer conduit 50. The proximal end of the rigid portion 50a preferably includes an enlarged, tubular handle 56 for improving maneuverability of the probe 16 during operation.

Figure 5:
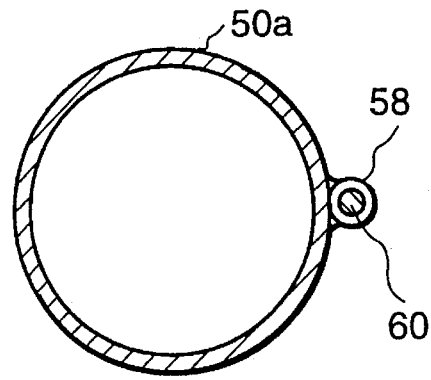
FIG. 5 is a cross sectional view through a transfer conduit in the probe illustrated in FIG. 3 and taken along line 5—5.

In order to minimize or prevent condensation of the high temperature pyrolysate vapors released into the hood 46 during operation, suitable means are provided for heating the entire transfer conduit 50 for maintaining a suitably high temperature therein for maintaining the efficacy of the pyrolysate 38 to be analyzed. More specifically, the rigid portion 50a of the transfer conduit 50 as illustrated in FIGS. 2, 3, and 5 includes a relatively small rigid conduit 58 such as stainless steel suitably secured by welding for example to the rigid portion 50a of the transfer conduit 50 which may also be stainless steel. Inside the conduit 58 is a conventional, electrically insulated, resistive heating element or wire 60 which extends from the hood 46 and through the handle 56. The heating wire 60 is suitably electrically joined to a conventional power supply 62 (see FIG. 2) which preferably provides 110 AC voltage thereto for heating the wire 60. As shown in FIG. 2, the flexible portion 50b of the transfer conduit 50 preferably is spirally wound with a conventional flexible heating element or wire 64 which extends its entire length from the handle 56 and preferably over the membrane separator 54 for effectively heating those components as well. The flexible portion 50b may be formed of a suitable high temperature material such as stainless steel. And, the separator 54 may be primarily stainless steel. The heating wire 64 is also preferably joined to the power supply 62, and both heating wires 60, 64 may be formed of nichrome or other suitable electrically resistive heating element material. The heating wires 60, 64 are preferably operated for maintaining a suitably high temperature (for example, about 200° C.) within the transfer conduit 50.

Figure 4:
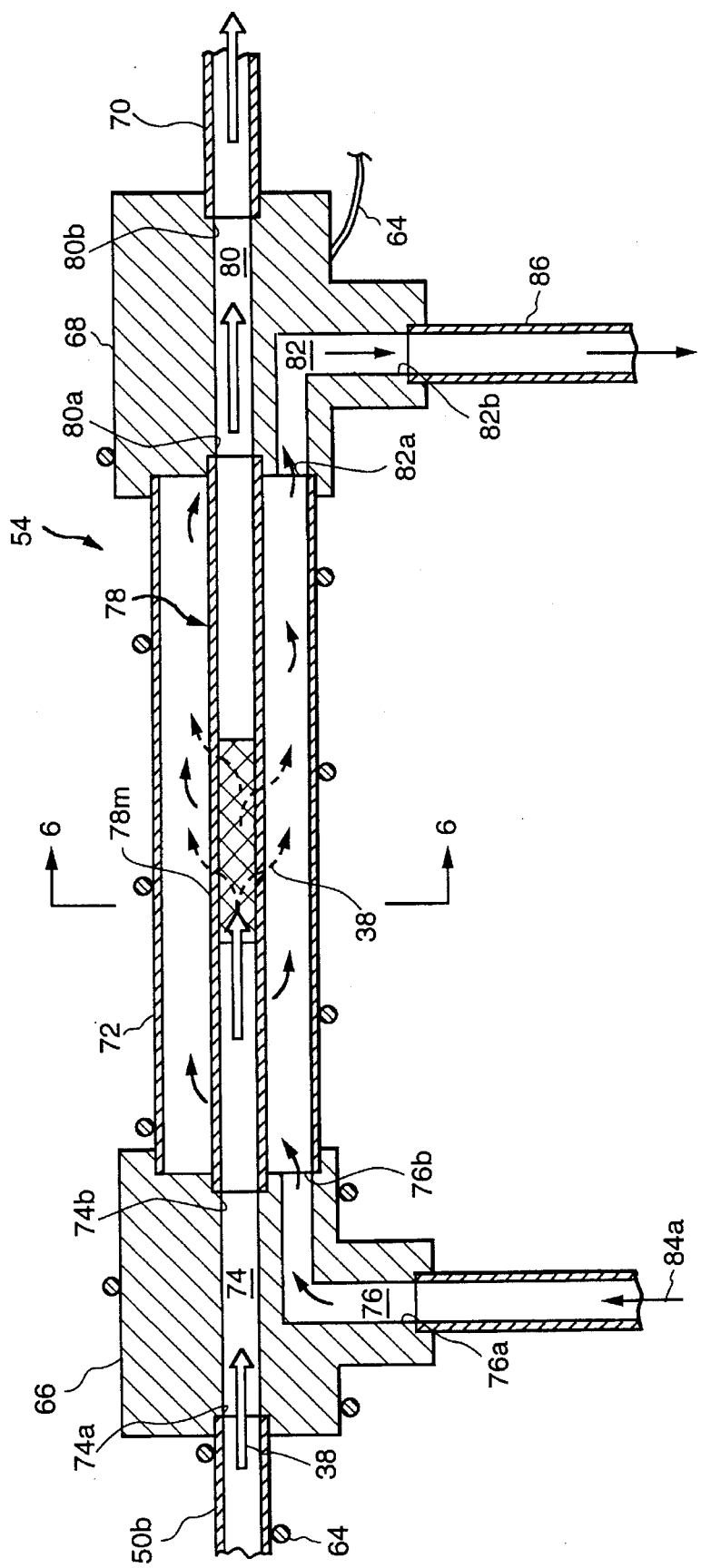
FIG. 4 is an elevational, sectional view of the membrane separator illustrated in FIG. 2.

Prior to analyzing the pyrolysate 38, it is desirable to separate any gaseous or particulate contaminates therein which is accomplished using the membrane separator 54 illustrated in a preferred embodiment in FIGS. 2 and 4. The separator 54 includes an inlet fitting 66 joined in flow communication with the outlet end of the flexible transfer conduit portion 50b, and an outlet fitting 68 spaced from the inlet fitting 66 and joined in flow communication with the pump 52 by a suitable conduit 70. An outer flow tube 72 extends between the inlet and outlet fittings 66, 68.

As illustrated in FIG. 4, the inlet fitting 66 includes primary and secondary independent inlet flow channels 74, 76 therein having first inlet and outlet ports 74a, 74b and second inlet and outlet ports 76a, 76b, respectively. The first inlet port 74a is disposed in flow communication with the outlet end of the flexible portion 50b of the transfer conduit 50 for receiving the pyrolysate 38 therefrom. An inner separator tube 78 is disposed concentrically inside the outer tube 72, with one end thereof disposed in flow communication with the first outlet port 74b for receiving the pyrolysate 38 from the transfer conduit 50.

The outlet fitting 68 similarly includes primary and secondary independent outlet flow channels 80, 82 therein having third inlet and outlet ports 80a, 80b and fourth inlet and outlet ports 82a, 82b, respectively. The downstream end of the separator tube 78 is disposed in flow communication with the third inlet port 80a, and in turn in flow communication with the pump 52 through the third outlet port 80b. In this way, the pyrolysate 38 is channeled directly through the inlet fitting 66 and through the separator tube 78 by the vacuum drawn from the pump 52 connected to the outlet fitting 68.

The outer tube 72 is spaced from and surrounds the separator tube 78 to define a tubular plenum therearound and extends between the inlet and outlet fittings 66, 68, and is disposed in flow communication with the second outlet port 76b and the fourth inlet port 82a. Means are provided for channeling an inert transport gas such as helium through the outer tube 72 around the separator tube 78 therein via the secondary inlet and outlet flow channels 76, 82 of the inlet and outlet fittings 66, 68. As shown in FIG. 2, a conventional gas supply 84 is disposed in flow communication with the second inlet port 76a for providing the transport gas 84a thereto and through the secondary inlet channel 76 into the outer tube 78 as illustrated in FIG. 4. A return conduit 86 as shown in FIG. 2 is disposed in flow communication with the fourth outlet port 82b for channeling the transport gas 84a with portions of the pyrolysate 38 therein picked up from the separator tube 78 inside the outer tube 72 for discharge from the secondary outlet channel 82 for flow through the return conduit 86 to a conventional spectrochemical analyzer 88 in which the pyrolysate 38 is analyzed for its chemical composition.

Figure 6:
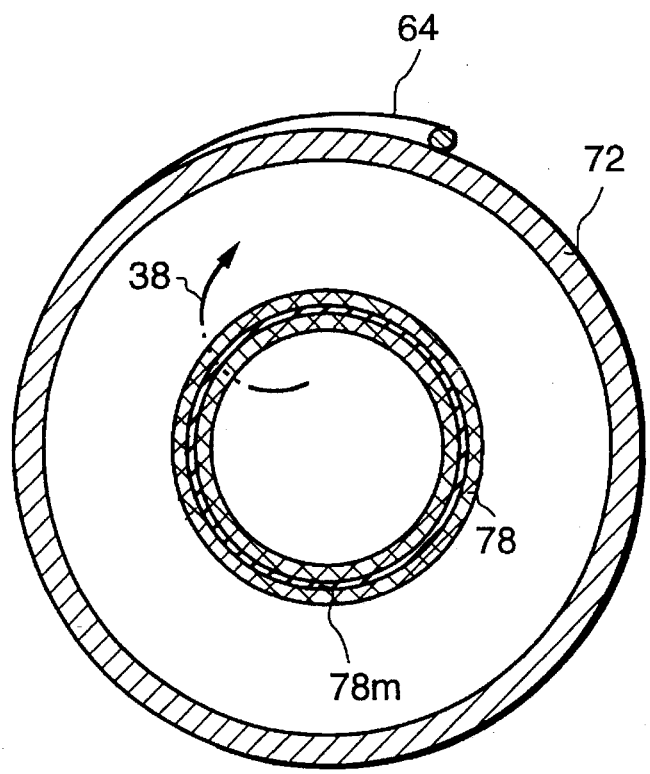
FIG. 6 is a cross sectional view through the membrane separator of FIG. 4 and taken along line 6—6.
Figure 7:
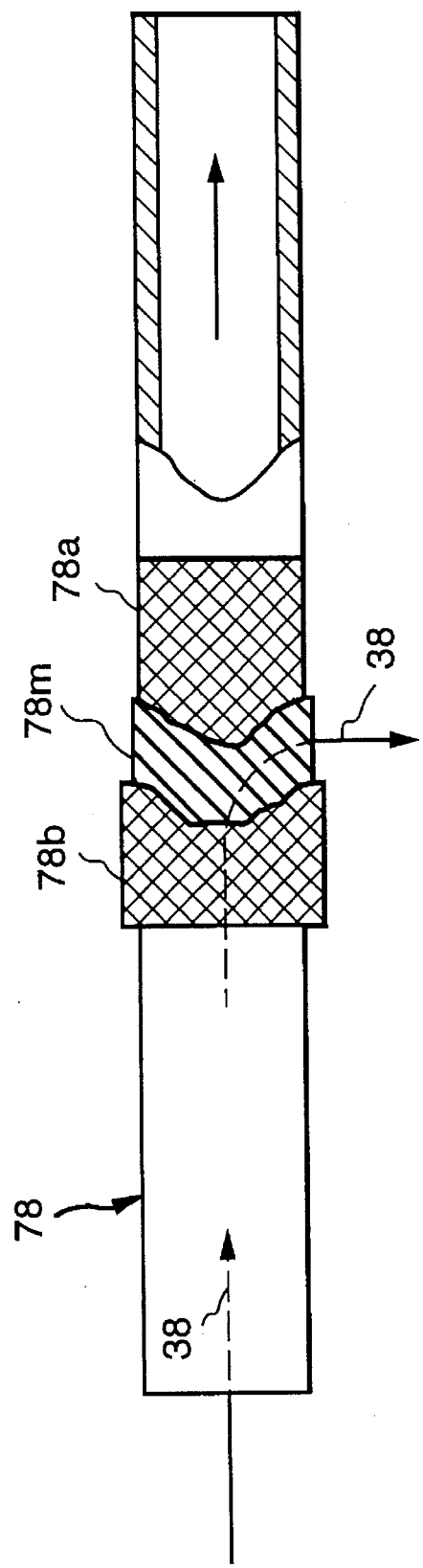
FIG. 7 is a partly sectional, layered view of a tube separator used in the membrane separator illustrated in FIG. 4.

The separator tube 78 as illustrated in FIG. 4 includes a tubular separator membrane 78m on a central portion thereof which is effective for passing the pyrolysate 38 therethrough from inside the separator tube 78 to outside the separator tube 78 and inside the outer tube 72 while separating the contaminates therefrom. FIGS. 6 and 7 illustrate in more particularity the separator tube 78 in an exemplary embodiment having a first tubular porous mesh or wire screen 78a disposed at the central portion of the tube 78 between two solid, tubular end portions. The separator membrane 78m is a solid, tubular member suitably supported or formed directly on the first mesh 78a and sealingly joined thereto by molding for example. A second tubular porous mesh 78b preferably surrounds the membrane 78m for allowing the pyrolysate 38 to pass therethrough from the membrane 78m. The membrane 78m may be formed of any suitable conventional material such as solid silicone sheets, e.g. polydimethylsiloxane. The pyrolysate 38 is soluble in the polydimethylsiloxane used for the membrane 78m, and dissolves therein and passes therethrough to be carried by the transport gas 84a inside the outer tube 72. The membrane 78m is suitably sized for each application, and for example may be about 25 mm long with an outer diameter of about 10 mm. Accordingly, the separator membrane 78m is effective for allowing the pyrolysate 38 to pass therethrough and separate therefrom undesirable contaminates such as particulates, and (in part) gases such as water vapor and $CO_2$. In an alternate embodiment, the membrane 78m may be simply impregnated into the first mesh 78a without need for the second mesh 78b if desired. The meshes 78a and 78b and their end supports are preferably stainless steel for example since the separator tube 78 and the outer tube 72 are preferably maintained at high temperature in the range of about 200°–250° C. for example.

As illustrated in FIG. 2, the pyrolysate 38 is carried by the transport gas 84a through the return conduit 86 to a conventional analytical cell 88a of the spectrochemical analyzer 88 which is preferably an infrared spectrometer for example. In an alternate embodiment, the spectrochemical analyzer 88 could be a mass spectrometer if desired. The spectrochemical analyzer 88 is conventionally effective for producing a spectrum of the pyrolysate 38 for determining the chemical composition thereof as is conventionally known. The analysis time for a single pyrolysate sample 38 may be in the order of about 10 seconds.

In operation, the probe 16 illustrated in FIG. 3 is positioned next to the specimen 12, with the wire cutting portion 20c being heated to a suitable temperature so that as it contacts the specimen 12, the specimen 12 is pyrolyzed by cutting or melting thereof to release the pyrolysate 38 therefrom. The pyrolysate 38 is collected in the hood 46 by the vacuum created by the pump 52 (see FIG. 2) which draws both the pyrolysate 38 and ambient air 40 through the hood 46 and through the heated transfer conduit 50. in the membrane separator assembly 54 illustrated in FIG. 4, the pyrolysate 38 is separated from the air 40 and any contaminates carried therewith by being dissolved through the membrane 78m for flow into the outer tube 72. The pyrolysate 38 is then carried by the transport gas 84a through the return conduit 86 to the spectrochemical analyzer 88 in which its chemical composition may be determined.

Upon completion of one analysis, the wire 20 as illustrated in FIG. 3 may be indexed by powering the motor 28m to rotate the drive reel 28 to index into position a clean cutting portion 20c of the wire 20 for the next pyrolysis. The wire cutting portion 20c may then be heated to the required temperature so that it may be placed against another specimen 12 for releasing the pyrolysate 38 therefrom which again is carried to the membrane separator 54 in which the pyrolysate 38 is transferred to the transport gas 84*a* for flow to the spectrochemical analyzer 88 in a subsequent analysis thereof. In this way, the wire 20 may be repeatedly indexed for pyrolyzing in turn different ones of the specimens 12, and conducting in turn spectrochemical analysis of each of the different specimens in a relatively quick and efficient process as the conveyor belt 14 illustrated in FIG. 1 carries the specimens 12 therealong.

After continued use of the pyrolysis instrument 10, the supply of wire 20 on the feed reel 26 illustrated in FIG. 3 for example will become exhausted at which time the drive wheel 28 can be replaced with an empty drive wheel, and the empty feed reel 26 with a full feed reel. Furthermore, and referring to FIG. 4, the separator tube 78 may require replacement from time to time, and therefore, the outer tube 72 may be removed for allowing removal and replacement of the inner separator tube 78 therein. FIG. 4 illustrates schematically the sealed joints of both the inlet and outlet fittings 66, 68. The joints may take any suitable and conventional form for allowing disassembly of the components for access to and replacement of the separator tube 78 itself. For example, the various tubes illustrated in FIG. 4 may contain conventional ferrules at the ends thereof which provide effective sealed joints when compressed in corresponding hollow nuts. One type of suitable joint is identified under the trademark SwageLok.

What is claimed is:

1. A method for obtaining a pyrolysate from a polymer specimen comprising:

positioning a portion of a wire against said specimen;

heating said wire to pyrolyze by cutting said specimen to release said pyrolysate therefrom;

separating gases and particulate contaminants therein from said pyrolysate;

indexing into position another portion of said wire for effecting a subsequent pyrolysis; and collecting said pyrolysate produced from pyrolysis of said specimen by said heated wire.

2. A method according to claim 1 further comprising conducting spectrochemical analysis of said separated pyrolysate to determine chemical composition thereof.

3. A method according to claim 2 further comprising:

repeatedly indexing said wire and positioning further polymer specimens adjacent thereto for conducting in turn spectrochemical analysis of each of said different specimens.

* * * * *